US010987080B2

(12) United States Patent
Nakamura

(10) Patent No.: US 10,987,080 B2
(45) Date of Patent: Apr. 27, 2021

(54) RADIATION IRRADIATION DETECTION SYSTEM AND RADIATION GENERATION APPARATUS

(71) Applicant: FUJIFILM CORPORATION, Tokyo (JP)

(72) Inventor: Kenji Nakamura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 229 days.

(21) Appl. No.: 15/949,092

(22) Filed: Apr. 10, 2018

(65) Prior Publication Data
US 2018/0303450 A1 Oct. 25, 2018

(30) Foreign Application Priority Data

Apr. 25, 2017 (JP) .............................. JP2017-086707

(51) Int. Cl.
*A61B 6/00* (2006.01)
*G01T 1/208* (2006.01)
(Continued)

(52) U.S. Cl.
CPC .............. *A61B 6/542* (2013.01); *G01T 1/208* (2013.01); *H04N 5/232* (2013.01); *H04N 5/32* (2013.01)

(58) Field of Classification Search
CPC .......... H04N 5/232; H04N 5/32; A61B 6/542; G01T 1/208
See application file for complete search history.

(56) References Cited

U.S. PATENT DOCUMENTS 6,782,077 B2 * 8/2004 Hirai ......................... A61B 6/06
378/154
2003/0086523 A1 * 5/2003 Tashiro ................ A61B 6/4233
378/19
(Continued)

FOREIGN PATENT DOCUMENTS

JP 2014-57831 A 4/2014
JP 2017-221328 A 12/2017

OTHER PUBLICATIONS

English language translation of the following: Office action dated Aug. 11, 2020 from the JPO in a Japanese patent application No. 2017-086707 corresponding to the instant patent application. This office action translation is submitted now in order to supplement the understanding of the cited reference which is being disclosed in the instant Information Disclosure Statement.

*Primary Examiner* — Dani Fox
*Assistant Examiner* — Soorena Kefayati
(74) *Attorney, Agent, or Firm* — SOLARIS Intellectual Property Group, PLLC

(57) ABSTRACT

A radiation irradiation detection system includes a radiation generation apparatus that includes a radiation generation unit, an emission control unit controlling emission of the radiation, and an exposure switch unit receiving a radiation irradiation instruction and a radiation stoppage instruction, and a radiation detection apparatus that includes a radiation detector detecting the radiation transmitted through a subject, and a detection control unit controlling the radiation detector, and the emission control unit starts emission of the radiation in a case where the emission permitting signal output from the detection control unit is received while the exposure switch unit is receiving the radiation irradiation instruction, continuously performs emission of the radiation regardless of a reception state of the emission permitting signal in a preset emission period after the radiation starts to (Continued)

be emitted, and stops emission of the radiation in a case where the instruction reception unit receives the radiation stoppage instruction.

2 Claims, 3 Drawing Sheets

(51) Int. Cl.
  *H04N 5/32* (2006.01)
  *H04N 5/232* (2006.01)

(56) References Cited

U.S. PATENT DOCUMENTS

| | | | | |
|---|---|---|---|---|
| 2008/0240355 | A1* | 10/2008 | Ohishi | A61B 6/4441 378/98 |
| 2012/0051510 | A1* | 3/2012 | Ohta | A61B 6/542 378/62 |
| 2012/0051522 | A1* | 3/2012 | Nishino | A61B 6/4411 378/108 |
| 2013/0077744 | A1* | 3/2013 | Kamiya | A61B 6/548 378/62 |
| 2013/0114793 | A1* | 5/2013 | Ohta | A61B 5/0059 378/63 |
| 2013/0148782 | A1* | 6/2013 | Tajima | A61B 6/4233 378/62 |
| 2013/0148784 | A1* | 6/2013 | Tajima | A61B 6/5294 378/62 |
| 2013/0208852 | A1* | 8/2013 | Koishi | A61B 6/548 378/19 |
| 2013/0279657 | A1* | 10/2013 | Hiroike | A61B 6/4241 378/62 |
| 2013/0279661 | A1* | 10/2013 | Tamura | A61B 6/4208 378/98 |
| 2014/0301536 | A1* | 10/2014 | Kim | A61B 6/40 378/91 |
| 2015/0055752 | A1* | 2/2015 | Takahashi | H04N 5/32 378/62 |
| 2015/0078528 | A1* | 3/2015 | Okada | H05G 1/44 378/97 |
| 2015/0139398 | A1* | 5/2015 | Tajima | H01L 27/14812 378/62 |
| 2015/0164459 | A1* | 6/2015 | Ito | G01T 1/2018 378/97 |
| 2015/0164461 | A1* | 6/2015 | Imamura | H05G 1/44 378/97 |
| 2015/0363926 | A1* | 12/2015 | Enomoto | A61B 6/542 382/132 |
| 2015/0378030 | A1* | 12/2015 | Tamura | H04N 5/32 378/98.2 |
| 2016/0025865 | A1* | 1/2016 | Wayama | A61B 6/542 250/370.07 |
| 2016/0029986 | A1* | 2/2016 | Nishii | A61B 6/4233 250/394 |
| 2016/0029991 | A1* | 2/2016 | Tajima | A61B 6/461 378/98 |
| 2016/0151031 | A1* | 6/2016 | Watanabe | A61B 6/5294 378/98.5 |
| 2016/0262715 | A1* | 9/2016 | Charnegie | A61B 6/542 |
| 2016/0296190 | A1* | 10/2016 | Suzuki | A61B 6/5241 |
| 2020/0037426 | A1* | 1/2020 | Uchiyama | A61B 6/542 |

* cited by examiner

RADIATION IRRADIATION DETECTION SYSTEM AND RADIATION GENERATION APPARATUS

CROSS REFERENCE TO RELATED APPLICATIONS

The present application claims priority under 35 U.S.C. § 119 to Japanese Patent Application No. 2017-086707 filed on Apr. 25, 2017. The above application is hereby expressly incorporated by reference, in its entirety, into the present application.

BACKGROUND OF THE INVENTION

Technical Field

The present invention relates to a radiation irradiation detection system which emits radiation toward a subject and detects radiation transmitted through the subject, and a radiation generation apparatus in the radiation irradiation detection system.

Related Art

In the related art, there has been proposed a radiation irradiation detection system configured to include a radiation generation apparatus provided with an X-ray tube and the like, and a radiation detection apparatus provided with a radiation detector such as a flat panel detector (FPD) detecting radiation which is output from the radiation generation apparatus and is transmitted through a patient.

In such a radiation irradiation detection system, a preparation operation of the radiation detector is controlled by periodically resetting electric charge signals accumulated by leaking currents while radiation is not applied. During starting of radiation irradiation, preparation operation control transitions to electric charge accumulation control. In the electric charge accumulation control, an electric charge signal corresponding to a dose of radiation transmitted through a patient is accumulated in each pixel of a radiation image detector.

In order to cause the radiation detector to transition from the preparation operation control to the electric charge accumulation control according to the starting of radiation irradiation as mentioned above, the radiation generation apparatus and the radiation detection apparatus are required to be synchronized with each other.

As a method of synchronization between the radiation generation apparatus and the radiation detection apparatus, for example, a method is proposed in which a signal for permitting radiation to be emitted is transmitted from the radiation detection apparatus to the radiation generation apparatus in a wired or wireless manner, the radiation detection apparatus starts to emit radiation in a case where the emission permitting signal is received, and the radiation detector starts an electric charge accumulation operation.

For example, JP2014-57831A proposes that, in a radiation generation apparatus having an exposure switch which receives radiation irradiation instruction, in a case where a logical product of an irradiation instruction from the exposure switch and the emission permitting signal is true, radiation is emitted from the radiation generation apparatus.

However, for example, in a case where an emission permitting signal is transmitted from a radiation detection apparatus to a radiation generation apparatus as a wireless communication signal, the emission permitting signal may not be normally received by the radiation generation apparatus due to, for example, the influence of noise.

In this case, as described above, in a case where emission of radiation is controlled on the basis of a logical product of the emission permitting signal output from the radiation detection apparatus and the irradiation instruction from the exposure switch, the emission permitting signal cannot be normally received, and thus emission of radiation is stopped. In other words, capturing of a radiation image is wrongly stopped although the radiation image can be normally captured. Therefore, reimaging is required to be performed, and thus there is a problem in that a radiation exposure dose of a patient increases.

SUMMARY

The present invention has been made in light of the problem, and an object thereof is to provide a radiation irradiation detection system and a radiation generation apparatus capable of reducing a radiation exposure dose of a patient without performing unnecessary reimaging.

According to the present invention, there is provided a radiation irradiation detection system including a radiation generation apparatus that includes a radiation generation unit generating radiation, an emission control unit controlling emission of the radiation, and an instruction reception unit receiving a radiation irradiation instruction and a radiation stoppage instruction; and a radiation detection apparatus that includes a radiation detector detecting the radiation transmitted through a subject, and a detection control unit controlling the radiation detector, in which the detection control unit outputs an emission permitting signal for permitting the radiation to be emitted to the radiation generation apparatus, and in which the emission control unit starts emission of the radiation in a case where the emission permitting signal is received while the instruction reception unit is receiving the radiation irradiation instruction, and continuously performs emission of the radiation regardless of a reception state of the emission permitting signal in a preset emission period after the radiation starts to be emitted, and stops emission of the radiation in a case where the instruction reception unit receives the radiation stoppage instruction.

In the radiation irradiation detection system of the present invention, the emission control unit may stop emission of the radiation only in a case where the instruction reception unit receives the radiation stoppage instruction.

In the radiation irradiation detection system of the present invention, each of the radiation generation apparatus and the radiation detection apparatus may include a wireless communication unit that performs wireless communication, and the wireless communication unit of the radiation detection apparatus may output the emission permitting signal, and the wireless communication unit of the radiation generation apparatus may receive the emission permitting signal.

In the radiation irradiation detection system of the present invention, in a case where the instruction reception unit receives the radiation irradiation instruction, and a preparation operation of the radiation detector is finished, the detection control unit may output the emission permitting signal, and may start an operation of accumulating a detection signal of the radiation in the radiation detector.

In the radiation irradiation detection system of the present invention, the radiation generation apparatus is preferably portable.

According to the present invention, there is provided a radiation generation apparatus including a radiation generation unit that generates radiation; an emission control unit that controls emission of the radiation; and an instruction reception unit that receives a radiation irradiation instruction and a radiation stoppage instruction, in which the emission control unit starts emission of the radiation in a case where an emission permitting signal output from a radiation detection apparatus detecting the radiation transmitted through a subject is received while the instruction reception unit is receiving the radiation irradiation instruction, and continuously performs emission of the radiation regardless of a reception state of the emission permitting signal in a preset emission period after the radiation starts to be emitted, and stops emission of the radiation in a case where the instruction reception unit receives the radiation stoppage instruction.

The radiation generation apparatus of the present invention is preferably portable.

According to the radiation irradiation detection system and the radiation generation apparatus of the present invention, the emission control unit starts emission of the radiation in a case where the emission permitting signal is received while the instruction reception unit is receiving the radiation irradiation instruction, and continuously performs emission of the radiation regardless of a reception state of the emission permitting signal in a preset emission period after the radiation starts to be emitted.

Consequently, imaging can be prevented from being wrongly stopped as described above, and thus it is possible to reduce a radiation exposure dose of a patient without performing unnecessary reimaging. Since emission of the radiation is stopped in a case where the instruction reception unit receives the radiation stoppage instruction, it is possible to appropriately stop emission of the radiation by using the instruction reception unit in a case where emission of the radiation is required to be stopped for some reason.

DETAILED DESCRIPTION

Figure 1:
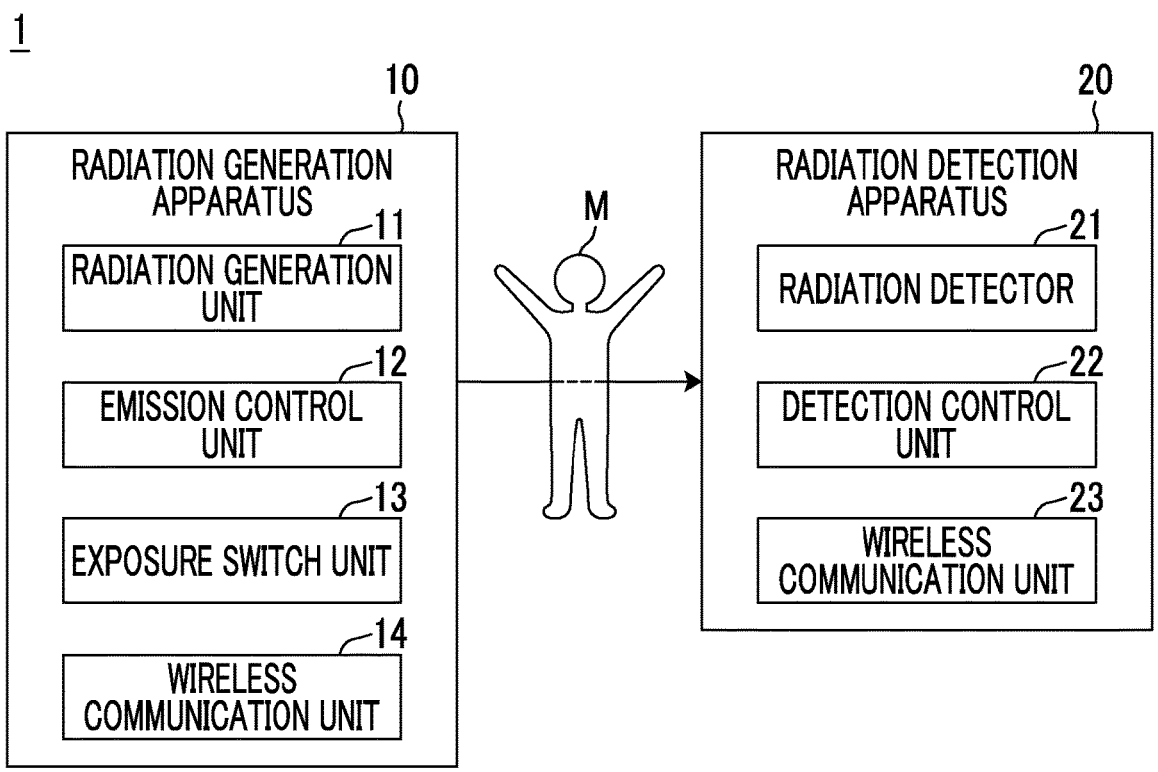
FIG. 1 is a block diagram illustrating a schematic configuration of a radiation irradiation detection system according to an embodiment of the present invention.

Hereinafter, a radiation irradiation detection system and a radiation generation apparatus according to an embodiment of the present invention will be described in detail with reference to the drawings. FIG. 1 is a block diagram illustrating a schematic configuration of a radiation irradiation detection system of the present embodiment.

A radiation irradiation detection system 1 of the present embodiment includes, as illustrated in FIG. 1, a radiation generation apparatus 10 and a radiation detection apparatus 20. The radiation generation apparatus 10 is preferably portable, and the radiation detection apparatus 20 is also preferably a portable cassette. However, the present invention is not limited to a portable radiation irradiation detection system, and is applicable to an installation type radiation irradiation detection system such as a radiation irradiation detection system imaging a standing subject and a radiation irradiation detection system imaging a lying subject.

The radiation generation apparatus 10 emits radiation toward a subject M such as a patient, and includes a radiation generation unit 11 which generates radiation, an emission control unit 12 which controls emission of radiation, an exposure switch unit 13 (corresponding to an instruction reception unit of the present invention), and a wireless communication unit 14.

The radiation generation unit 11 includes a radiation source such as an X-ray tube, and generates radiation by applying a high voltage thereto.

The emission control unit 12 includes, for example, a central processing unit (CPU), and controls emission of radiation from the radiation generation apparatus 10. Specifically, the emission control unit 12 controls a tube voltage and a tube current applied to the radiation generation unit 11, and controls the intensity and an emission time of radiation emitted from the radiation generation unit 11 by controlling the tube voltage or the tube current.

The emission control unit 12 of the present embodiment starts emission of radiation in a case where an emission permitting signal output from a detection control unit 22 which will be described later of the radiation detection apparatus 20 is received while the exposure switch unit 13 is receiving a radiation irradiation instruction. The emission permitting signal is a signal for permitting radiation to be emitted. In the present embodiment, the emission permitting signal is output to the radiation generation apparatus 10 from the detection control unit 22 from a time point at which a preparation operation of a radiation detector 21 of the radiation detection apparatus 20 is completed.

In the present embodiment, the emission permitting signal is transmitted from a wireless communication unit 23 of the radiation detection apparatus 20 as a wireless signal and is received by the wireless communication unit 14 of the radiation generation apparatus 10, but the emission permitting signal may not be normally received by the radiation generation apparatus 10 due to, for example, the influence of noise.

In this case, as described above, in a case where emission of radiation is controlled on the basis of the emission permitting signal output from the radiation detection apparatus 20, and an irradiation instruction from the exposure switch unit 13, the emission permitting signal cannot be normally received, and thus emission of radiation is stopped in the related art. In other words, capturing of a radiation image is wrongly stopped although the radiation image can be normally captured. In a case where imaging is stopped as mentioned above, reimaging is required to be performed, and thus there is a problem in that a radiation exposure dose of a patient increases.

Therefore, in the present embodiment, emission of radiation is continuously performed regardless of a reception state of the emission permitting signal in a preset emission period after the radiation starts to be emitted, and the emission of the radiation is stopped only in a case where the exposure switch unit 13 receives a stoppage instruction. Consequently, as described above, even in a case where the emission permitting signal cannot be normally received by the radiation generation apparatus 10, radiation is continuously emitted without being changed, and capturing of a radiation image can be completed. Therefore, unnecessary reimaging is not performed, and thus it is also possible to reduce a radiation exposure dose of a patient.

In a case where emission of radiation is required to be stopped for some reason, emission of radiation is stopped by receiving a stoppage instruction via the exposure switch unit 13. In the present embodiment, emission of radiation is stopped in response to only reception of a stoppage instruction via the exposure switch unit 13, but, for example, in a case where an emission stopping instruction is received via an emergency stoppage switch or the like, emission of radiation may be stopped.

The emission control unit 12 may monitor only a stoppage instruction using the exposure switch unit 13 of reception states of the stoppage instruction using the exposure switch unit 13 and the emission permitting signal after emission of radiation is started, and may control stoppage of emission of radiation assuming that the emission permitting signal is continuously normally received.

As described above, the wireless communication unit 14 receives the emission permitting signal transmitted from the wireless communication unit 23 of the radiation detection apparatus 20.

The exposure switch unit 13 receives a radiation irradiation instruction and a radiation stopping instruction given by a user. Specifically, in the present embodiment, an irradiation instruction is given by turning on the exposure switch unit 13, and an emission stopping instruction is given by turning off the exposure switch unit 13.

Next, the radiation detection apparatus 20 will be described. The radiation detection apparatus 20 includes the radiation detector 21, the detection control unit 22, and the wireless communication unit 23.

The radiation detector 21 detects radiation which is output from the radiation generation apparatus 10 and is transmitted through the subject M, and outputs a radiation detection signal. As the radiation detector 21, for example, a radiation detector including a scintillator (phosphor) which converts incident radiation into visible light, and a thin film transistor (TFT) active matrix substrate may be used. The radiation detector 21 is not limited thereto, and a so-called direct conversion type radiation detector which directly converts incident radiation into an electric charge signal may be used.

Figure 2:
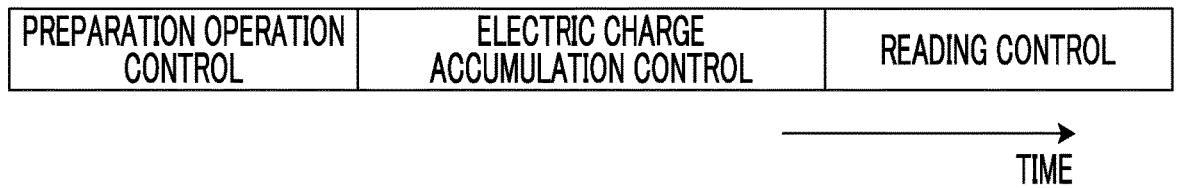
FIG. 2 is a diagram for explaining operation control for a radiation detector.

The detection control unit 22 includes, for example, a CPU, and controls an operation of the radiation detector 21. Operation control of the radiation detector 21 includes preparation operation control, electric charge accumulation control, and reading control as illustrated in FIG. 2.

In a period of the preparation operation control, a high voltage is applied to the radiation detector 21, and a preparation operation is performed such that the radiation detector 21 is brought into a state of being capable of detecting radiation.

The detection control unit 22 starts the electric charge accumulation control in a case where the exposure switch unit 13 is turned on and thus receives an irradiation starting signal after the preparation operation is completed. Specifically, the detection control unit 22 controls the radiation detector 21 to start accumulation of electric charge generated by irradiation with radiation transmitted through the subject M. The detection control unit 22 outputs an emission permitting signal to the radiation generation apparatus 10 from a time point at which the electric charge accumulation control is started. The emission control unit 12 causes radiation to be emitted in a case where an irradiation starting instruction is received by turning on the exposure switch unit 13, and the emission permitting signal is received. Radiation transmitted through the subject M is detected by the radiation detector 21. Emission of radiation is performed in only a preset emission period as long as an emission stopping instruction is not received via the exposure switch unit 13.

The detection control unit 22 starts the reading control from a time point at which the radiation emission period is finished. Specifically, the detection control unit 22 controls the radiation detector 21 to start reading of the electric charge signals accumulated in the radiation emission period. Radiation detection signals corresponding to the electric charge signals read from the radiation detector 21 are stored in a storage medium such as a memory provided in the radiation detection apparatus 20. The radiation detection signals stored in the storage medium undergo predetermined signal processing, and are output to an apparatus such as a console.

The wireless communication unit 23 transmits a radiation emission permitting signal and a radiation emission stopping signal to the radiation generation apparatus 10 as described above.

Figure 3:
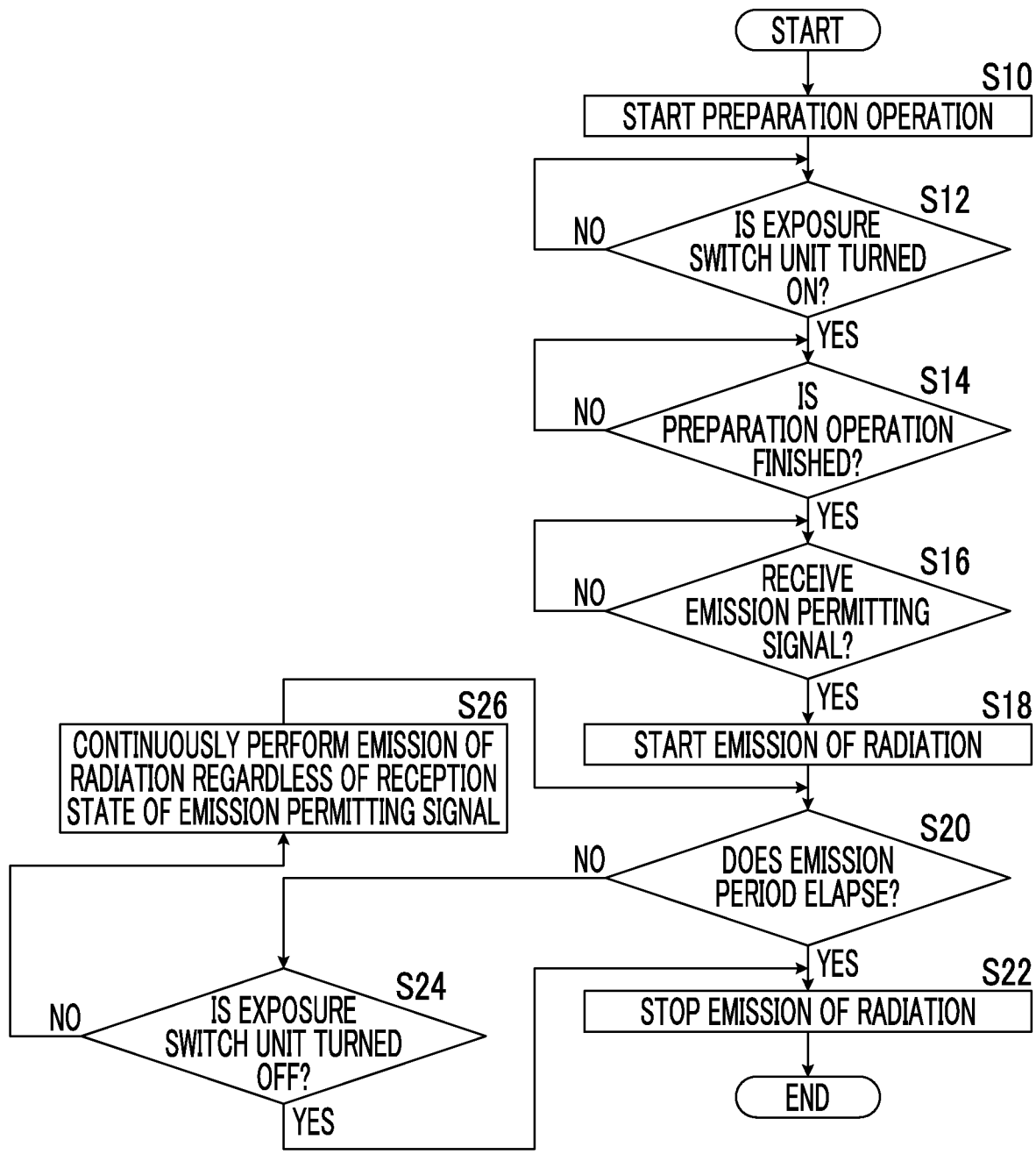
FIG. 3 is a flowchart for explaining an operation of the radiation irradiation detection system according to the embodiment of the present invention.
Figure 4:
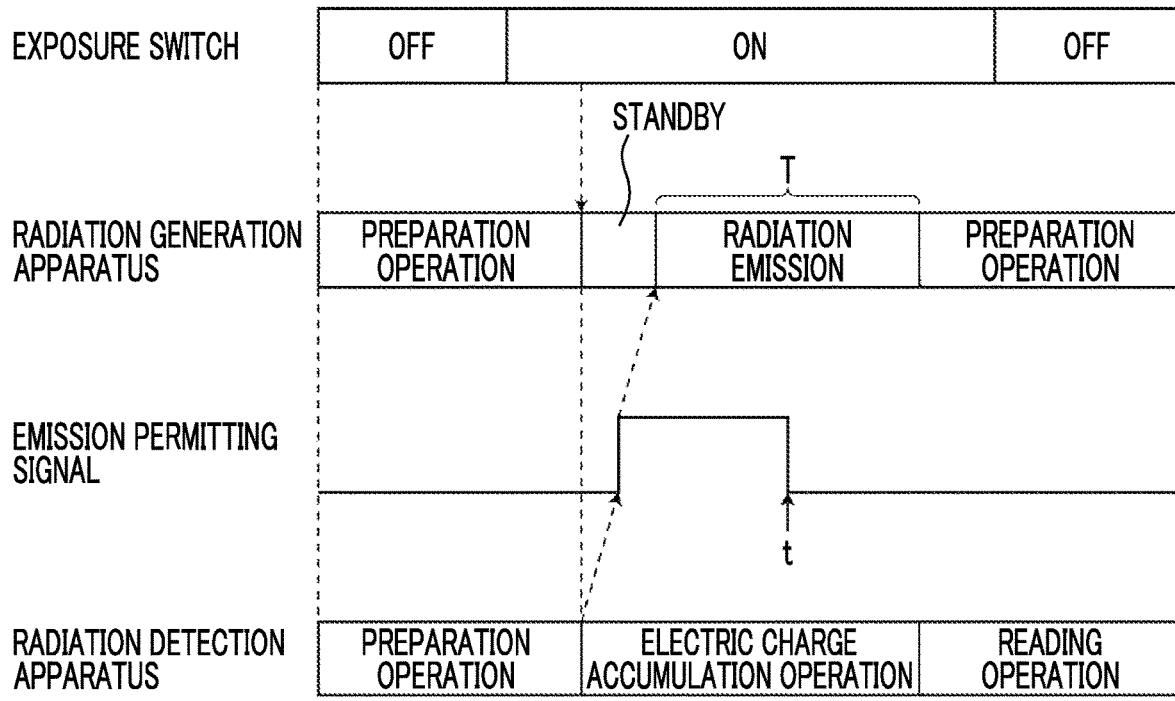
FIG. 4 is a timing chart illustrating an operation of the radiation irradiation detection system according to the embodiment of the present invention.
Figure 5:
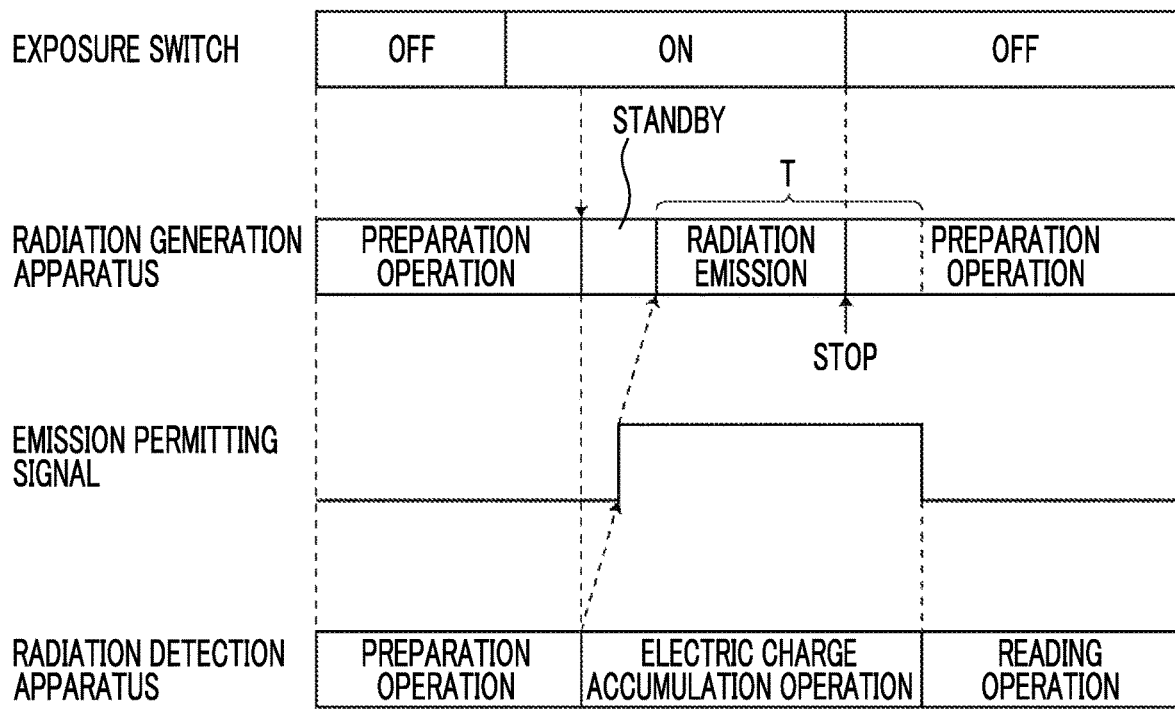
FIG. 5 is a timing chart illustrating an operation of the radiation irradiation detection system according to the embodiment of the present invention.

Next, a description will be made of an operation of the radiation irradiation detection system of the present embodiment with reference to a flowchart of FIG. 3 and timing charts of FIGS. 4 and 5. FIG. 4 is a timing chart in a case where an emission permitting signal cannot be normally received during a preset radiation emission period, but the exposure switch unit 13 is still turned on, and FIG. 5 is a timing chart in a case where a radiation stoppage instruction is received via the exposure switch unit 13 during the preset radiation emission period.

First, in the radiation generation apparatus 10, a preparation operation of the radiation generation unit 11 is started by the emission control unit 12, and, in the radiation detection apparatus 20, a preparation operation of the radiation detector 21 is started under the control of the detection control unit 22 (S10).

In a case where the subject M is located at a position with respect to the radiation detector 21, and then the exposure switch unit 13 is turned on by a radiologist or the like (S12, YES), it is checked whether or not the preparation operations of the radiation generation unit 11 and the radiation detector 21 are finished (S14).

In a case where it is checked that the preparation operations of the radiation generation unit 11 and the radiation detector 21 are finished (Second wireless communication unit 14, YES), the detection control unit 22 of the radiation detection apparatus 20 starts to output an emission permitting signal to the radiation generation apparatus 10, and starts an electric charge accumulation operation in the radiation detector 21.

In a case where the emission permitting signal is received in the radiation generation apparatus 10 (S16), the emission control unit 12 starts to emit radiation (S18).

Next, it is checked whether or not the exposure switch unit 13 is turned off in a preset radiation emission period T (S20, NO), and, in a case where the exposure switch unit 13 is still turned on (S24, NO), the emission control unit 12 causes radiation to be continuously emitted regardless of a reception state of the emission permitting signal in the radiation generation apparatus 10 (S26). In other words, as illustrated in FIG. 4, for example, even in a case where the emission permitting signal is not normally received from a time point t in the preset radiation emission period T, radiation is continuously emitted as long as the exposure switch unit 13 is in an ON state.

In a case where the radiation emission period T elapses before the exposure switch unit 13 is turned off (S20, YES), the emission control unit 12 stops emission of radiation (S22). The detection control unit 22 finishes the electric charge accumulation operation in the radiation detector 21, and performs the reading control.

On the other hand, in a case where the exposure switch unit 13 is turned off (S24, YES) in the preset radiation emission period T (S20, NO), as illustrated in FIG. 5, the emission control unit 12 stops emission of radiation even in a case where the emission permitting signal is normally received (S22).

In a case where the exposure switch unit 13 is turned off, and thus radiation imaging is stopped, the detection control unit 22 may stop an operation of the radiation detector 21, and may finish an electric charge accumulation operation in the radiation detector 21 so as to perform a reading operation as usual. As mentioned above, an operation as usual is performed, and a radiation image is acquired, and thus it is possible to determine whether or not reimaging is required to be performed.

In the radiation irradiation detection system of the embodiment, an emission permitting signal is transmitted and received through wireless communication, but wired communication may be used.

An emission permitting signal which is output from the radiation detection apparatus 20 to the radiation generation apparatus 10 may be a consecutive signal as illustrated in FIGS. 4 and 5, and may be a pulsed signal with a preset cycle.

What is claimed is:

1. A radiation irradiation detection system comprising:
    a radiation generation apparatus that includes:
        a radiation generation unit generating radiation,
        an emission control unit controlling emission of the radiation, and
        an exposure switch unit receiving a radiation irradiation instruction and
    a radiation stoppage instruction; and
    a radiation detection apparatus that includes:
        a radiation detector detecting the radiation transmitted through a subject, and
        a detection control unit controlling the radiation detector,
    wherein the detection control unit outputs an emission permitting signal for permitting the radiation to be emitted to the radiation generation apparatus,
    wherein, in a case in which the exposure switch unit receives the radiation irradiation instruction, and a preparation operation of the radiation detector is finished, the detection control unit outputs the emission permitting signal and starts an operation of accumulating a detection signal of the radiation in the radiation detector,
    wherein the emission control unit:
        starts emission of the radiation in a case in which the emission permitting signal is received while the exposure switch unit is receiving the radiation irradiation instruction, and
        determines whether or not the exposure switch unit is turned off in a preset radiation emission period after the radiation starts to be emitted, and, in a case where the exposure switch unit is still turned on,
        continuously performs emission of the radiation regardless of a reception state of the emission permitting signal in a preset emission period after the radiation starts to be emitted, and stops emission of the radiation in a case in which the exposure switch unit receives the radiation stoppage instruction,
    wherein the emission control unit stops emission of the radiation only in a case in which the exposure switch unit receives the radiation stoppage instruction.

2. The radiation irradiation detection system according to claim 1,
    wherein each of the radiation generation apparatus and the radiation detection apparatus includes a wireless communication unit that performs wireless communication, and
    wherein the wireless communication unit of the radiation detection apparatus outputs the emission permitting signal, and the wireless communication unit of the radiation generation apparatus receives the emission permitting signal.

* * * * *